United States Patent [19]

Brill

[11] 4,115,420
[45] Sep. 19, 1978

[54] CATALYTIC CONVERSION OF THALLIUM (I) TO THALLIUM (III)

[75] Inventor: William F. Brill, Skillman, N.J.

[73] Assignee: Halcon International, Inc., New York, N.Y.

[21] Appl. No.: 789,053

[22] Filed: Apr. 21, 1977

Related U.S. Application Data

[63] Continuation-in-part of Ser. No. 740,143, Nov. 8, 1976, abandoned, which is a continuation-in-part of Ser. No. 691,115, May 28, 1976, abandoned.

[51] Int. Cl.$^2$ .............................................. C07F 5/00
[52] U.S. Cl. ............................. 260/429 R; 423/395; 423/495; 423/544; 423/659
[58] Field of Search .................. 260/429 R; 423/395, 423/495, 544, 659

[56] References Cited

U.S. PATENT DOCUMENTS

| | | | |
|---|---|---|---|
| 3,399,956 | 9/1968 | Hirose et al. | 423/295 |
| 3,717,670 | 2/1973 | Schultz | 260/476 R |

OTHER PUBLICATIONS

Spencer, L. Anorg. Chem., V44, pp. 399–407, (1905).
Spencer, L. Anorg. Chem., V44, pp. 379–399, (1905).
Kruse, et al., J. Org. Chem. V36, pp. 36–37, (1971).

Primary Examiner—Helen M. S. Sneed
Attorney, Agent, or Firm—William C. Long; David Dick; Jack B. Murray, Jr.

[57] ABSTRACT

A monovalent thallium compound is converted to a trivalent thallium compound by treating the thallium (I) compound with molecular oxygen in the presence of a Group VIII noble metal catalyst to oxidize the thallium (I) compound to a thallium (III) compound.

13 Claims, No Drawings

CATALYTIC CONVERSION OF THALLIUM (I) TO THALLIUM (III)

RELATED APPLICATIONS

This is a continuation-in-part of application Ser. No. 740,143, filed Nov. 8, 1976, now abandoned which in turn is a continuation-in-part of application Ser. No. 691,115, filed May 28, 1976 now abandoned.

This invention relates to the oxidation of thallium (I) to thallium (III).

Trivalent thallium compounds, i.e., thallic compounds, have been used as oxidizing agents in various reactions. For example, Kruse et al., J. Org. Chem. 36, 1154 (1971) describe the epoxidation of certain olefins with thallic acetate and in co-pending application Ser. No. 679,584, filed Apr. 23, 1976, now U.S. Pat. No. 4,021,453, it is disclosed that thallic aryl carboxylates are surprisingly effective as epoxidation agents.

In all of these reactions the trivalent thallium is reduced to the monovalent state and if the thallium is to be reused in the reaction it is necessary to reoxidize or "regenerate" it by converting thallium (I) to thallium (III). Various methods for effecting this conversion have been proposed and are more or less effective. Thus, J. F. Spencer, Z. Anorg. Chem. vol. 44, pages 379, 399–405 (1905) discloses the oxidation of thallous nitrate to the thallic state using molecular oxygen in a 1 N. acid solution in the presence of a platinum plate which had been coated with platinum black. However, such a process resulted in a conversion of only 1 to 2% of the thallous nitrate to the thallic state, and is therefore only of academic interest. Moreover, such a low conversion was obtained only after repeated polarization of the platinum plate. Hirose et al., U.S. Pat. No. 3,399,956 describes the oxidation of Tl(I) to Tl(III) by means of molecular oxygen in an acidic aqueous medium containing a chloride or bromide ion and an ion of a redox metal such as copper, mercury, chromium, manganese, iron, cobalt, and nickel. Hirose et al. refer to earlier processes for effecting the conversion of Tl(I) to Tl(III) and point out the problems involved in achieving the desired oxidation and the disadvantages and drawbacks of prior procedures. While the Hirose et al process is described as an improvement over processes previously proposed, it is limited to the use of aqueous chloride or bromide solutions so that the thallium (III) is always produced as a chloride or bromide and it is generally necessary to use the redox metal in large amounts in relation to the thallium compound being treated.

It is, accordingly, an object of the present invention to provide an improved process for the oxidation of monovalent thallium to trivalent thallium.

It is a further object of the invention to provide a process of the character indicated which is not limited to specific reaction media.

In accordance with the invention, a monovalent thallium compound is converted to a trivalent thallium compound by treating the thallium (I) compound with molecular oxygen in the presence of a Group VIII noble metal catalyst in a fluid medium to oxidize the thallium (I) compound to a thallium (III) compound in a rapid and efficient manner.

The Group VIII noble metals comprise platinum, palladium, rhodium, ruthenium, osmium and iridium, all of which may be used as catalysts in the process of this invention but platinum, palladium, ruthenium and rhodium are preferred, especially platinum and palladium. Mixed catalysts can be used if desired. The catalyst is preferably used in a heterogenous system, i.e., in the form of a suspension in the reaction medium and in this case the catalyst is ordinarily supported upon a solid carrier, but it is also possible to use the catalyst in a homogenous system, i.e., it may be employed in a form which is soluble in the reaction medium. Thus, the Group VIII noble metal catalyst may be suitably added as a compound of the above-mentioned metals, preferably on a carrier, but is is possible to add the catalyst as the finely-divided metal, e.g., platinum black, or as the metal supported on a carrier. In the case of a homogenous system, the metal is eventually converted to a compound sufficiently soluble to provide a catalytic amount of the metal in solution in the reaction mixture. The nature of the compound of the Group VIII noble metal is not critical and any convenient compound may be used. For example, typical compounds include the oxides, the inorganic salts such as the salts of mineral acids, e.g., the chlorides and oxychlorides, the iodides, the fluorides, the phosphates, the sulfates and the sulfites, the sulfides, and the hydroxides. Other typical compounds include salts of organic acids such as acetates or other carboxylates, organo-metallic compounds such as tetramethyl platinum, carbonyls and carbonyl halides. Also various chelates, association compounds and enol salts may be used. Further illustrative of such compounds are palladium acetate, rhodium chloride, platinum oxide (Adams catalyst), chloroplatinic acid, platinum tetrachloride, platinum diamino dinitrite, platinum cyanide, sodium tetrachloro platinite, potassium tetrachlo platinate, platinum dicarbonyl dichloride, platinum acetyl acetonacetate, tetrakis (triphenyl phosphine) platinum, tetramine platinum chloride, and corresponding compounds of the other Group VIII noble metals.

When the Group VIII noble metal catalyst is supported upon a carrier, the carrier or substrate which is employed is suitably in the form of a porous solid of such size that it can be readily dispersed in the liquid reaction medium, e.g., from 400 mesh/inch to ½-inch particle sizes. Such carrier materials are exemplified by pumice, alumina, silica, silica-alumina, magnesia, diatomaceous earth, bauxite, titania, zirconia, clays, both natural and acid treated such as Super-Filtrols, attapulgus clay (attapulgite), lime, magnesium silicate, silicon carbide, activated and unactivated carbons, zeolites as well as the zeolitic molecular sieves, solid foams, such as ceramic honeycombs, and porous organic polymers. The above carriers are suitably used in the form of regular and irregular particles such as tubes, balls, broken pieces, and the like. Such supported forms of the Group VIII noble metals and their compounds are prepared by conventional methods, e.g., deposition from a solution, for example as described in Schultz U.S. Pat. No. 3,717,670 in connection with rhodium compounds and, indeed, many such supported catalysts are available commercially, particularly in the case of the zero valent free metal.

Concentrations of the Group VIII noble metal component on the support can vary widely but illustrative concentrations lie within the range of 0.1 to 20 wt. %. Higher concentrations may, however, be used if desired.

The ratio of catalyst to monovalent thallium compound used in the process of the invention can also vary over a wide range. For example 1 to 40 mols of catalyst per 100 mols of monovalent thallium compound are advantageously used, but lesser or greater amounts may be employed if desired, the upper limit being determined only by economic considerations and the lower limit only by the amount which will be catalytically effective. In any case, it is a feature of the invention that only catalytic quantities are required to bring about a rapid conversion.

Ordinarily, the higher the reaction temperature, the greater the reaction rate. It is unnecessary, however, to employ high temperatures. Normally, the reaction temperature may range from room temperature to about 150° C. Typically, temperatures of 20° C. to 100° C. are used, but higher or lower temperatures are operable but excessively high temperatures are not advantageous because they may eventually result in reaction between the thallium compounds and the solvent. Total pressure is not a specific parameter of the process and atmospheric or superatmospheric pressures may be employed but desirably oxygen partial pressures above the reaction mixture of at least 2 psi, preferably 500 to 1000 psi are provided and higher oxygen partial pressures, e.g., up to 10,000 psi can be used, if desired. It is generally desirable to stir the reaction medium, particularly when a heterogenous catalyst is employed, and this may be effected by mechanical agitation, shaking, and like means known to the art.

Any convenient monovalent thallium compound can be treated in accordance with the invention. Typically, the compound will be a salt which may be organic, such as a carboxylate of an alkyl, cycloalkyl or aryl carboxylic acid containing up to 20 carbon atoms, such as an acetate or benzoate, or inorganic, such as a nitrate, a sulfate, or a halide, but other compounds may be used, if desired. The thallous compound is suitably one which is at least partly soluble in the liquid medium used.

The thallous compounds resulting from the epoxidation reactions described in the above-mentioned Kruse et al article and in U.S. Pat. No. 4,021,453, will be carboxylates and it is a feature of this invention that such thallous carboxylates can be converted to the thallic carboxylates with ease so that the conversion products can be directly recycled to the epoxidation reaction.

The reaction medium for the conversion of monovalent thallium to trivalent thallium can be aqueous or non-aqueous. Non-aqueous media comprise organic solvents of various types as are well known to the art, including both polar and non-polar solvents, but the polar solvents are particularly preferred. Typical polar organic solvents include the carboxylic acids such as acetic acid, ethers such as tetrahydrofuran and p-dioxane, alcohols such as t-butyl alcohol and methanol, ether alcohols such as polyglycols, nitriles such as acetonitrile, amides such as dimethylformamide, ketones such as acetone, polar chlorinated hydrocarbons such as chloroform, as well as dimethyl sulfoxide, and the like. Non-polar solvents include the hydrocarbons and chlorinated hydrocarbons such as carbon tetrachloride. It will be understood that a solvent is preferably chosen which is not susceptible to oxidation under the particular conditions selected for the oxidation.

To achieve the improved conversions and yields to thallic compound of the present invention, liquid reaction media employed in this process should possess an initial pH of at least about 0.5, desirably at least about 1 and preferably at least about 2. Still higher conversions and yields are obtained by this invention when the pH is at least about 3. In liquid media having a pH greater than 7, the trivalent thallium produced will normally be converted into the hydroxide which will precipitate. However, this is not an impediment to the process disclosed herein since the hydroxide can be readily recovered and converted into any desired thallic salt in conventional manner, e.g., the hydroxide can be converted to a thallic salt by reaction with the appropriate acid. Therefore, there is no critical upper limit to the pH of the liquid reaction medium in the practice of the present invention, although a pH of greater than about 10 is generally uneconomic. The pH values given above for the liquid reaction media of the present invention are those determined by diluting an aliquot of the liquid reaction medium with an equal volume of water, and then measuring the pH of the resulting aqueous mixture at a temperature of 25° C. If a two-phase liquid results on dilution, the determining pH is that which is measured in the aqueous phase.

While water can be used as the sole reaction medium, or an organic solvent can be used as the sole reaction medium, it is preferred to use a water-polar organic solvent mixture containing up to about 50 volume percent water, typically 5–10% water.

If the pH of the liquid reaction medium is 7 or less and if an anion corresponding to the anion of the thallous compound is present, then a substantial portion of the thallic compound will be obtained in the form of a salt containing that anion. On the other hand, other thallic salts can be formed by supplying the appropriate anion, e.g., by adding nitric acid or a different carboxylic acid to the reaction mixture. For example, if the monovalent thallium is in the form of an acetate, then acetic acid is advantageously included in the reaction mixture so that all of the trivalent thallium will also be obtained in the form of the acetate. Sufficient acetic acid is of course present to provide the necessary molecular quantity. Similarly, if a benzoate is desired, then benzoic acid is added to the reaction medium. The thallium (III) compound can thus be obtained in various forms, as desired and, as mentioned, it can be in the same form as the thallium (I) compound supplied.

Thus, monovalent thallium compounds can be readily converted to trivalent thallium compounds, and the reaction medium containing the trivalent thallium compound produced can be used directly or after suitable treatment, such as filtration to remove the catalyst for epoxidation, or other reaction. The trivalent thallium compound can also be separated from the reaction medium by precipitation, evaporation of solvent, or the like, if desired.

The invention will be more fully understood by reference to the following examples of specific embodiments thereof but it will be understood that these examples are given for illustrative purposes only and are not intended as limitative of the invention. In the Examples, determinations of the thallium (III) product were carried out by means of conventional complexiometric analyses using standard ethylene nitrilo tetraacetic acid. The reaction mixture is analyzed in each case at the end of the indicated reaction period. Before analysis, the reaction mixture is filtered to separate the catalyst, and the filtered solids are washed with 0.5 N acetic acid. The combined filtrate is then subjected to analysis.

In the examples, pH values for the liquid reaction media are determined by diluting a sample of the liquid medium in each example with an equal volume of water and then measuring the pH of the resulting aqueous mixture (or the pH of the aqueous phase, if a two-phase liquid results on dilution) as described above, using a pH meter employing a combination glass electrode having an internal silver/silver chloride reference. The initial pH values determined for the examples are tabulated in Table 1.

EXAMPLE I

Into a 200 cc stirred autoclave is charged a 0.1N solution of thallium (I) acetate in 95 volume percent acetonitrile and 5 volume percent water, also containing acetic acid in 0.6N concentration, along with 0.026 mol per liter of platinum supported on alumina, the support containing 5% of the catalytic metal. The autoclave is pressured with molecular oxygen to 500 psig (25° C.) and then heated at 80° C. for 2 hours with continuous stirring. The reaction mixture is found to contain thallium (III) acetate in an amount corresponding to a conversion of 27%. In this and in the following examples the catalysts are commercially available products supplied by Chemical Division of Englehard Industries and/or the Alpha Products Division of the Ventron Corp. The stirred autoclave used in this example is also used as the reaction vessel in the following examples.

EXAMPLE II

The autoclave is charged with a 0.1N solution of thallium (I) acetate in acetonitrile also containing acetic acid in 0.3N concentration, together with 0.026 mol per liter of platinum in the form of the supported catalyst used in Example I. The autoclave is pressured with molecular oxygen to 500 psig (25° C.) and then heated at 80° C. for 2 hours with continuous stirring. The reaction mixture is found to contain thallium (III) acetate in an amount corresponding to a conversion of 31.5%.

EXAMPLE III

The autoclave is charged with a 0.1N solution of thallium (I) acetate in 95 volume percent propionitrile and 5 volume percent water, also containing acetic acid in 0.3N concentration, together with the catalyst used in Example I (0.026 mol per liter of platinum). The autoclave is pressured with molecular oxygen to 500 psig (25° C.) and then heated at 80° C. for 2 hours with continuous stirring. A conversion of 13% is determined.

EXAMPLE IV

The 200 cc stirred autoclave is charged with a 0.1N solution of thallium (I) acetate in 95 volume percent acetonitrile and 5 volume percent water, also containing acetic acid in 0.3N concentration, along with 0.05 mol per liter of platinum supported on alumina, the support containing 10% of the catalytic metal. The autoclave is pressured with molecular oxygen to 500 psig (25° C.) and then heated at 80° C. for 2 hours with continuous stirring. A conversion of 10% is determined.

EXAMPLE V

Into the autoclave is charged a 0.1N solution of thallium (I) acetate in 95 volume percent acetonitrile and 5 volume percent water, also containing acetic acid in 0.3N concentration, along with 0.05 mol per liter of platinum supported on activated carbon, the support containing 10% of the catalytic metal. The autoclave is pressured with molecular oxygen to 500 psig (25° C.) and then heated at 80° C. for 2 hours with continuous stirring. A conversion of 21% is determined.

EXAMPLE VI

Into the autoclave is charged a 0.1N solution of thallium (I) acetate in acetonitrile also containing acetic acid in 0.6N concentration, along with 0.026 mol per liter of platinum supported on alumina, the support containing 5% of the catalytic metal. The autoclave is pressured with molecular oxygen to 800 psig (25° C.) and then heated at 80° C. for 2 hours with continuous stirring. The reaction mixture is found to contain thallium (III) acetate in an amount corresponding to a conversion of 37%.

EXAMPLE VII

The autoclave is charged with a 0.1N solution of thallium (I) acetate in carbontetrachloride also containing acetic acid in 0.3N concentration, together with 0.026 mol per liter of platinum supported on alumina, the support containing 5% of the catalytic metal. The autoclave is pressured with molecular oxygen to 500 psig (25° C.) and then heated at 80° C. for 2 hours with continuous stirring. The reaction mixture is found to contain thallium (III) acetate in an amount corresponding to a conversion of 30%.

EXAMPLE VIII

Example VII is repeated except that the concentration of acetic acid is 0.6N and the pressure is 800 psig. A conversion of 33% is obtained.

EXAMPLE IX

Example VIII is repeated except that the time is extended to 4 hours. A conversion of 35% is obtained.

EXAMPLE X

The reactor is charged with a 0.1N solution of thallium (I) acetate in chloroform, also containing acetic acid in 0.3N concentration, along with 0.026 mol per liter of platinum supported on alumina, the support containing 5% of the catalytic metal. The autoclave is pressured with molecular oxygen to 500 pisg (25° C.) and then heated at 80° C. for 2 hours with continuous stirring. A conversion of 22.5% is obtained.

EXAMPLE XI

The autoclave is charged with a 0.1N solution of thallium (I) acetate in 95 volume percent acetonitrile and 5 volume percent water, also containing acetic acid in 0.3N concentration, along with 0.0256 mol per liter of platinum supported on alumina, the support containing 5% of the catalytic metal. The autoclave is pressured with air to 800 psig (25° C.) and then heated at 80° C. for 2 hours with continuous stirring. A conversion of 14.5% is obtained.

EXAMPLE XII

The autoclave is charged with a 0.1N solution of thallium (I) acetate in 95 volume percent acetonitrile and 5 volume percent water, also containing acetic acid in 0.3N concentration, along with 0.047 mol per liter of palladium supported on alumina, the support containing 5% of the catalytic metal. The autoclave is pressured with molecular oxygen to 500 psig (25° C.) and then heated at 80° C. for 2 hours with continuous stirring. A conversion of 22.5% is determined.

EXAMPLE XIII

Into the 200 cc stirred reactor is charged a 0.1N solution of thallium (I) acetate in 95 volume percent acetonitrile and 5 volume percent water, also containing acetic acid in 0.3N concentration, along with 0.026 mol per liter of platinum supported on alumina and 0.005 mol per liter of ruthenium supported on activated carbon, each support containing about 5% of the catalytic metal. The autoclave is pressured with molecular oxygen to 500 psig (25° C.) and then heated at 80° C. for 2 hours with continuous stirring. A conversion of 18.4% is obtained.

EXAMPLE XIV

The apparatus is charged with a 0.1N solution of thallium (I) acetate in 95 volume percent acetonitrile and 5 volume percent water, also containing acetic acid in 0.3N concentration, along with 0.05 mol per liter of rhodium supported on alumina, the support containing about 5% of the catalytic metal. The autoclave is pressured with molecular oxygen to 500 psig (25° C.) and then heated at 80° C. for 2 hours with continuous stirring. A conversion of 6.5% is determined.

EXAMPLE XV

The apparatus is again charged with a 0.1N solution of thallium (I) acetate in 95 volume percent acetonitrile and 5 volume percent water, also containing acetic acid in 0.3N concentration, along with 0.05 mol per liter of palladium supported on activated carbon, the support containing about 5% of the catalytic metal. The autoclave is pressured with molecular oxygen to 500 psig (25° C.) and then heated at 80° C. for 2 hours with continuous stirring. A conversion of 5.5% is determined.

EXAMPLE XVI

Into the stirred autoclave is charged a 0.1N solution of thallium (I) acetate in 90 volume percent acetonitrile and 10 volume percent water, also containing acetic acid in 0.3N concentration, together with 0.026 mol per liter of platinum supported on alumina, the support containing 5% of the catalytic metal. The autoclave is pressured with molecular oxygen to 500 psig (25° C.) and then heated at 80° C. for 2 hours with continuous stirring. A conversion of 20% is determined.

EXAMPLE XVII

Into the autoclave of Example I is charged a 0.1N solution of thallium (I) acetate in a solvent mixture of 17 volume percent acetonitrile, 77 volume percent tertiary butyl alcohol and 6 volume percent water, also containing acetic acid in 0.3N concentration, along with 0.026 mol per liter of platinum supported on alumina, the support containing 5% of the catalytic metal. The autoclave is pressured with molecular oxygen to 500 psig (25° C.) and then heated at 80° C. for 2 hours with continuous stirring. A conversion of 8% is determined.

EXAMPLE XVIII

The autoclave of Example I is charged with a 0.1N solution of thallium (I) acetate in a solvent mixture of 17 volume percent acetonitrile, 77 volume percent tetrahydrofuran, and 6 volume percent water, also containing acetic acid in 0.3N concentration, along with 0.026 mol per liter of platinum supported on alumina, the support containing 5% of the catalytic metal. The autoclave is pressured with molecular oxygen to 500 psig (25° C.) and then heated at 80° C. for 2 hours with continuous stirring. A conversion of 14% is obtained.

EXAMPLE XIX

Into the 200 cc stirred autoclave is charged a 0.1N solution of thallium (I) acetate in 95 volume percent dimethylformamide and 5 volume percent water, also containing acetic acid in 0.3N concentration, along with 0.026 mol per liter of platinum supported on alumina, the support containing 5% of the catalytic metal. The autoclave is pressured with molecular oxygen to 500 psig (25° C.) and then heated at 80° C. for 2 hours with continuous stirring. The reaction mixture is found to contain thallium (III) acetate in an amount corresponding to a conversion of 24%.

EXAMPLE XX

Into the autoclave is charged a 0.1N solution of thallium (I) acetate in acetonitrile also containing benzoic acid in 0.3N concentration, along with 0.026 mol per liter of platinum supported on alumina, the support containing 5% of the catalytic metal. The autoclave is pressured with molecular oxygen to 500 psig (25° C.) and then heated at 80° C. for 2 hours with continuous stirring. Analysis of the reaction mixture shows a 5% conversion to thallium (III) carboxylate.

EXAMPLE XXI

The autoclave is charged with a 0.1N solution of thallium (I) acetate in 95 volume percent acetonitrile and 5 volume percent water, also containing acetic acid in 0.3N concentration, along with 0.0256 mol per liter of platinum supported on alumina, the support containing 5% of the catalytic metal. The autoclave is pressured with molecular oxygen to 500 psig (25° C.) and then heated at 150° C. for 2 hours with continuous stirring. A conversion of 14% is determined.

EXAMPLE XXII

The autoclave is charged with a 0.1N solution of thallium (I) acetate in 95 volume percent acetonitrile and 5 volume percent water, also containing acetic acid in 0.3N concentration, along with 0.0256 mol per liter of platinum supported on alumina, the support containing 5% of the catalytic metal. The autoclave is pressured with molecular oxygen to 800 psig (25° C.) and then heated at 80° C. for 2 hours with continuous stirring. A conversion of 28.5% is obtained.

EXAMPLE XXIII

Into the apparatus is charged a 0.1N solution of thallium (I) acetate in 95 volume percent acetonitrile and 5 volume percent water, also containing acetic acid in 0.3N concentration, along with 0.0256 mol per liter of platinum supported on alumina, the support containing 5% of the catalytic metal. The autoclave is pressured with air to 800 psig (25° C.) and then heated at 80° C. for 2 hours with continuous stirring. A conversion of 14.5% is determined.

EXAMPLE XXIV

Into the autoclave is charged a 0.1N solution of thallium (I) acetate in 95 volume percent triethylene glycol dimethyl ether and 5 volume percent water, also containing acetic acid in 0.3N concentration, along with 0.0256 mol per liter of platinum supported on alumina, the support containing 5% of the catalytic metal. The autoclave is pressured with molecular oxygen to 1500 psig (25° C.) and then heated at 80° C. for 2 hours with continuous stirring. A conversion of 30.5% is obtained.

EXAMPLE XXV

Into the autoclave is charged a 0.05N solution of thallium (I) acetate in 95 volume percent acetonitrile and 5 volume percent water, also containing acetic acid in 0.3N concentration, along with 0.0256 mol per liter of platinum supported on alumina, the support containing 5% of the catalytic metal. The autoclave is pressured with molecular oxygen to 500 psig (25° C.) and then heated at 80° C. for 2 hours with continuous stirring. A conversion of 25% is obtained.

TABLE 1

| Example No. | pH | Example No. | pH |
|---|---|---|---|
| 1 | 5.3 | 14 | 5.2 |
| 2 | 5.2 | 15 | 5.2 |
| 3 | 5.2 | 16 | 5.2 |
| 4 | 5.2 | 17 | 5.1 |
| 5 | 5.2 | 18 | 5.2 |
| 6 | 5.1 | 19 | 5.4 |
| 7 | 4.5 | 20 | 5.2 |
| 8 | 3.7 | 21 | 5.2 |
| 9 | 4.5 | 22 | 5.2 |
| 10 | 4.3 | 23 | 5.2 |
| 11 | 5.2 | 24 | 5.2 |
| 12 | 5.2 | 25 | 5.5 |
| 13 | 5.2 | | |

While the process of the invention has been described above in terms of a liquid reaction medium, it will be obvious that it may be carried out in the vapor phase, the catalyst forming a bed through which the reactants are passed. It will also be apparent that various changes and modifications may be made without departing from the scope of the invention as defined in the appended claims and it is intended, therefore, that all matter contained in the foregoing description should be interpreted as illustrative only and not in a limiting sense.

What is claimed is:

1. A process for converting a thallium (I) compound to a thallium (III) compound which comprises reacting the thallium (I) compound with molecular oxygen in a liquid medium having a pH of at least about 1 and in the presence of a Group VIII noble metal.

2. A process as defined in claim 1, wherein the Group VIII noble metal is platinum or palladium.

3. A process as defined in claim 1, wherein the reaction is carried out under an oxygen partial pressure of 2 to 10,000 psi.

4. A process for converting a thallium (I) carboxylate to a thallium (III) carboxylate which comprises reacting the thallium (I) carboxylate with molecular oxygen in a liquid medium having a pH of from about 1 to 7 and in the presence of a Group VIII noble metal.

5. A process as defined in claim 1, wherein the thallium (I) compound is a carboxylate.

6. A process as defined in claim 1 wherein the liquid medium possesses a pH of at least about 2.

7. A process as defined in claim 1 wherein the liquid medium possesses a pH of at least about 3.

8. A process as defined in claim 4 wherein the liquid medium possesses a pH of from 2 to 7.

9. A process as defined in claim 4 wherein the liquid medium possesses a pH of from 3 to 7.

10. A process as defined in claim 4 wherein the Group VIII noble metal is platinum or palladium.

11. A process as defined in claim 4 wherein the reaction is carried out under an oxygen partial pressure of from 2 to 10,000 psi.

12. A process as defined in claim 4 wherein the thallium (I) carboxylate is derived from an alkyl, cycloalkyl or aryl carboxylic acid containing up to 20 carbon atoms.

13. A process as defined in claim 4 wherein the reaction is effected in the presence of a carboxylic acid.

* * * * *